United States Patent [19]

Hudson et al.

[11] 4,198,398

[45] Apr. 15, 1980

[54] ENKEPHALIN ANALOGUES

[76] Inventors: Derek Hudson, 23A Elm Rd., Wembley, Middlesex; Robert Sharpe, 99 King House, Ducane Rd., London W12 OHS; Michael Szelke, 10 North Drive, Ruislip, Middlesex, all of England

[21] Appl. No.: 923,478

[22] Filed: Jul. 10, 1978

[30] Foreign Application Priority Data

Jul. 12, 1977 [GB] United Kingdom ............... 29207/77
Dec. 8, 1977 [GB] United Kingdom ............... 51159/77

[51] Int. Cl.$^2$ ..................... A61K 37/00; C07C 103/52
[52] U.S. Cl. ............................. 424/177; 260/112.5 R
[58] Field of Search .................. 424/177; 260/112.5 R

[56] References Cited
PUBLICATIONS

Biological Abstract 1978, pp. 41745, vol. 66.

*Primary Examiner*—Delbert R. Phillips
*Attorney, Agent, or Firm*—Larson, Taylor and Hinds

[57] ABSTRACT

Compounds corresponding in structure to enkephalin or polypeptide analogues thereof, wherein one or more peptide links of the enkephalin or analogue is represented by a group or groups the same or different selected from dimethylene, methylene-imino and ketomethylene groups.

26 Claims, No Drawings

ENKEPHALIN ANALOGUES

BACKGROUND

The invention relates to enkephalin analogues or as they are also referred to herein, isosteres.

Enkephalin is the pentapeptide H-Tyr-Gly-Gly-Phe-Met-OH (methionine enkephalin), and since its discovery a great deal of work has been done synthesising analogues with a view to elucidation of the mode of action of enkephalin itself and in particular to clinical use of the analogues.

Much of this work has been specifically in varying the amino acids incorporated, or in analogues where nitrogen atoms replace carbon in the structure of the chain. However we, in seeking compounds with desirable stability in the body and useful biological activity, have used a new approach in which, essentially, we make modifications at the peptide bonds.

THE INVENTION

Accordingly there are now provided compounds corresponding in structure to enkephalin, or polypeptide analogues thereof possibly containing further residues wherein one or more of the peptide groups

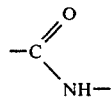

are represented by a group or groups, the same or different, selected from dimethylene —CH$_2$—CH$_2$—, methylene-imino —CH$_2$—NH— or —CH$_2$—NR— and keto-methylene

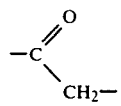

groups (R is an aliphatic protective group e.g. methyl, ethyl, propyl, cyclopropyl, butyl, allyl or the like).

A general formula for such compounds is for example:

R—Tyr—X—Gly—B—Y—Z where
(a)
— X is Gly or any D-amino acid residue particularly D-Ala or D-Met
— M is Phe or N-methyl Phe, as such or substituted with hydroxy or halogen in the aromatic ring
— Y is any D- or L-amino acid residue particularly Leu, Met the most preferred, or the sulphoxide of Met, Pro or Hypro, or formal derivatives thereof in which the oxygen of the terminal carboxyl carbon is replaced by hydrogen

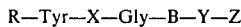

— Z is NHR or OR
(b)
the

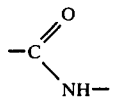

link between one or more pairs of residues is replaced by a group or groups, the same or different, selected from —CH$_2$—CH$_2$, —CH$_2$—NR— and

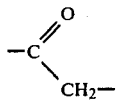

optionally with further modification by replacement of one or more remaining

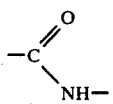

groups by

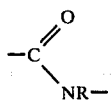

(c)
R is H or as above

The compounds in which the amino acid residue or derivative Y has a terminal amide group are generally more useful, being resistant to natural carboxypeptidases. For the same reason the D-acids are preferred to the L-acids.

It will be understood that any of the compounds may be in salt form or suitably protected at amino or other groups. Bare reference to a compound in the claims includes reference to the compound in such form.

Among 'hydrocarbon' isosteres two particular compounds, both representing replacement of a peptide link by dimethylene, are:

H—Tyr—NH—(CH$_2$)$_4$—CO-Phe-Met-NH$_2$.HCl in which the Gly-Gly residues of enkephalin are replaced by a 5-amino-valeric acid residue:

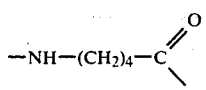

and another example is:

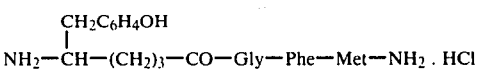

in which the Tyr-Gly residues of enkephalin are replaced by the residue:

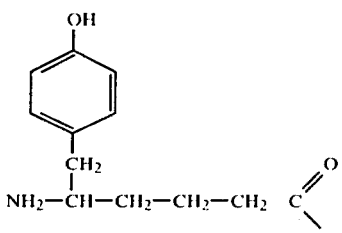

The acid giving this residue is available from protected derivatives of tyrosine, for example:

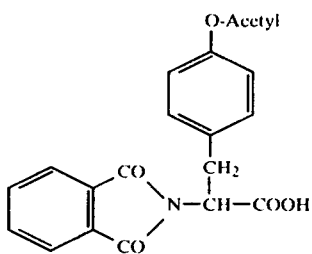

by repeated application of the Arndt-Eistert reaction.
Further particular compounds are:

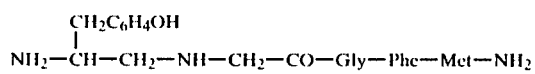

and the corresponding Metol compound (Examples 3 and 4), representing replacement of Tyr-Gly peptide link by a methylene-imino group, and:

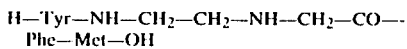

and the corresponding Metol and Met—NH$_2$ compounds (Examples 6, 7 and 8), representing a similar replacement but of the Gly-Gly peptide link.

Still another particular compound (Example 5) is:

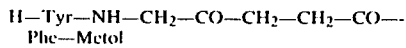

representing replacement of Gly-Gly peptide link by a ketomethylene group.

Activity

Significant brain radio receptor assay activity is, shown by the analogues, and numerical results are given below. Activity is also shown in the guineapig ileum system, which is known to correlate with human analgesic properties, and in the mouse vas deferens system.

The test results referred to above, with Met-Enkephalin for comparison, are:

| Analogue | Activity Relative to Met Enkephalin | | |
|---|---|---|---|
| | G.P.I | M.V.D. | R.R.A. |
| H211 (Tyr$^1$-Gly$^2$) HC isostere NH$_2$ | 3% | 0.9% | 8% |
| H212 (Gly$^2$-Gly$^3$) HC isostere NH$_2$ | <0.3% | 0.2% | <4% |
| H215 (Try$^1$-Gly$^2$) reduced -Enk NH$_2$ | 56% | N.D | 50% |
| H216 | | | |

-continued

| Analogue | Activity Relative to Met Enkephalin | | |
|---|---|---|---|
| | G.P.I | M.V.D. | R.R.A. |
| (Try$^1$-Gly$^2$) reduced -Enkol H218 | 83% | N.D. | 200% |
| (Gly$^2$-Gly$^3$) reduced Enk H219 | <1% | N.D. | N.D. |
| (Gly$^2$-Gly$^3$) reduced Enkol H220 | 0.3% | N.D. | N.D. |
| (Gly$^2$-Gly$^3$) reduced Enk-NH$_2$ (Comparison) | 0.3% | N.D. | N.D. |
| Met Enkephalin | 100% | 100% | 100% |

Notes
(i)G.P.I stands for guinea pig ileum
(ii)M.V.D. stands for mouse vas deferens
These assays were performed as described in the literature Hughes J., Kosterlitz, H.W. & Leslie, F.M. Br. J. Pharmac. 53, 371-381, 1968
Kosterlitz, H.W., and Watt, A.J., Br. J. Pharmac. Chemother., 33, 266–276 (1968)
(iii)R.R.A. stands for radio receptor assay; based on the concentration required to displace 50% of tritiated naloxone from rat brain membranes. The replacements were carried out against ($^3$H)-naloxone (1nM) in 0.1 M sodium chloride/50mM Tris buffer at pH 7.4; incubations were for 15 minutes in the absence of bacitracin. For general reference to the method see literature as discussed in "Opiate Receptor Mechanisms", S.H. Snyder and S. Matthysse eds, MIT Press, 1975.

We further have indications that the analogues stimulate release of prolactin and growth hormone from the pituitary. Reference to release by certain known enkephalin analogues is given in L. Cusan, A. Dupont, G. S. Kledzik, F. Labrie, D. H. Coy, A. Schally, *Nature* 268, 544 (1977).

Also, we have indications of in vivo analgesic effects of the analogues. The two compounds H211 and H212 cause analgesia lasting for several minutes when administered intraventricularly to rats, as determined by the tail flick assay (Ref. D'Amour, F. E., Smith, D. L., *J. Pharm.* 72, 74–79 (1941).)

Besides these results we have favourable indications of a considerable range of activities, in some of which a relatively low activity in the above brain membrane displacement or guinea pig ileum tests is an advantage in that other activities can be made use of without excessive opiate effect. The activities as a whole are:

| CNS (Central Nervous System) Activity | Analgesic, anaesthetic, sedative, hypnotic, psychotropic and behavioural effects, particularly the first and last of these |
|---|---|
| Neuro-Endocrine Activity | Affecting the release of hormones from the pituitary gland in particular GH (growth hormone) and prolactin |
| Peripheral Effects | Interaction with intestinal or other peripheral receptors, e.g. in suppression of diarrhoea |

Broadly the invention gives the potential compared with enkephalin itself of increased stability in the body, with therefore a prolonged duration of effect and possible intranasal and/or oral administration, and of variations in properties giving increased selectivity or potency and improved pharmaco-kinetics and/or pharmacodynamics.

General Discussion of Syntheses

An example is included of a general method of synthesis of "keto" analogues and hydrocarbon analogues derived from them, and also an alternative and simpler synthesis of a particular -Gly-Gly- derivative by a route not generally suitable and Tyr-Gly hydrocarbon analogues by repeated Arndt Eistert reaction.

"Keto" analogues are peculiarly useful because not only do they confer stability to the modified bond, but they also stabilise the adjacent peptide bond by forming a conjugated tautomeric form The general method for preparation of "keto" and "hydrocarbon" isosteres is given schematically below and then discussed briefly:

Summary scheme
'A'

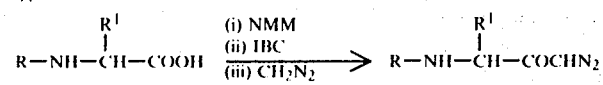

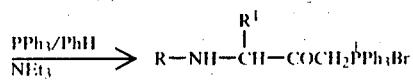 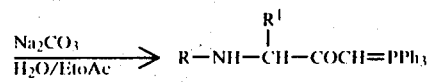

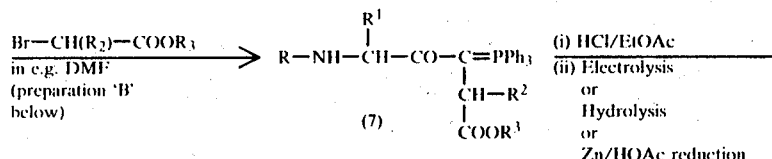

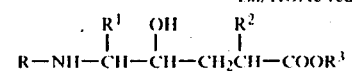

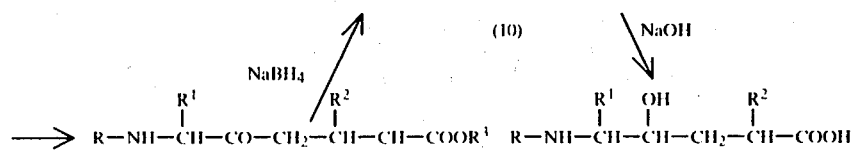

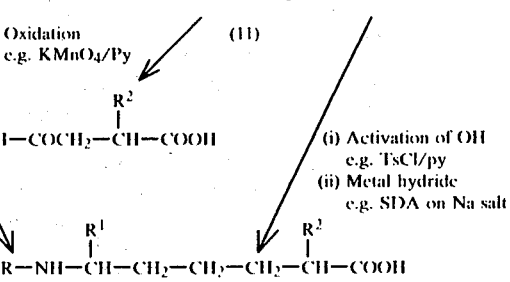

'B'

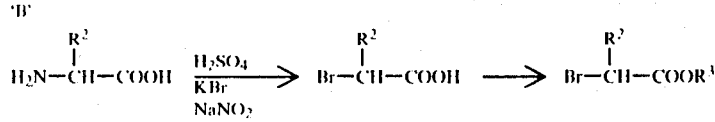

Key
R = Any suitable N-protecting group e.g. t-butoxycarbonyl

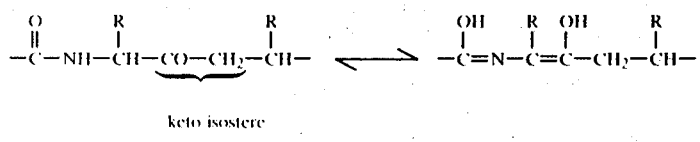

keto isostere

This stabilisation is manifested for example in a low tyrosine value obtained in acid hydrolysis of H222 (Example 5)

"Reduced isosteres" (i.e. methylene imino) may be synthesised by a variety of routes including reduction (Examples 3 and 4, H215 and H216) but also by substitution as with Examples 6 to 8, H218-220, and details of the synthesis of these last examples are included.

DMF = dimethylformamide
NMM = N-methylmorpholine
IBC = isobutylchloroformate
TsCl/py = tosyl chloride in pyridine
SDA = sodium dihydro-bis(2-methoxyethoxy) aluminate Thus for Gly-Phe isosteres:-

$R^2=CH_2C_6H_5$ and for Gly-Gly isosteres as in Example 5, H222) $R^1=R^2=H$

Thus amino acid (1) protected at the N-terminal and if necessary in the side chain $R^1$ is first converted into its diazoketone by treatment with N-methylmorpholine, isobutylchloroformate and diazomethane. An alternative is simply to treat the acid chloride with diazomethane. Then the diazoketone is treated with hydrogen bromide in ethyl acetate to give the α-bromoketone (2). This ketone is then treated with triphenyl phosphine in the presence of triethylamine, giving the α-ketophosphonium salt which in turn is converted to the ylide (3) by treatment with sodium carbonate.

Separately, the amino acid (4) which is to form the carboxyl terminal of the isostere, with its side chain $R^2$ protected if necessary, is converted to the corresponding α-bromo acid (5) by treatment with sulphuric acid, potassium bromide and sodium nitrite, and the bromo acid is then converted to its ester (6) by treatment with a diazo alkane $R^3CHN_2$.

The ylide (3) is then alkylated by reaction with ester (6) in a solvent such as dimethylformamide to give a new ylide (7), from which the triphenyl phosphine moiety is removed in per se known manner by electrolysis, hydrolysis, or zinc/acetic acid reduction. The product is an ester (8) of the keto-isostere, which can be converted to the free N-(and side chain) protected keto-isostere (9) by hydrolysis.

Alternatively the ester can be selectively reduced, for example with sodium borohydride, to the corresponding hydroxy compound (11). This hydroxy compound, after hydrolysis, can be re-oxidised to the keto-isostere if required, for example by alkaline potassium permanganate, or it can be converted to the N-(and side chain) protected hydrocarbon isostere (12) by activation of the hydroxyl group with tosyl chloride in pyridine and its subsequent removal with a metal hydride such as sodium dihydro-bis(2-methoxyethoxy) aluminate.

A further and preferred route to the hydrocarbon isostere is from the keto-isostere ester (8) via the keto-isostere itself, by direct reaction of the keto-isostere with tosylhydrazine followed by reduction with sodium borohydride.

DETAILED SYNTHESES—ENKEPHALIN

Solid phase peptide synthesis is the preferred method.

A 1.4% crosslinked 100-200 mesh resin prepared by copolymerisation of acetoxystyrene (10 mole %), styrene and divinylbenzene is for example suitable, after deacetylation.

The following description is of a preparation by successive reaction cycles of enkephalin itself, illustrating steps useful in the preparation of the analogues of the invention. The phenolic resin was generated by overnight treatment of the acetoxy resin with excess hydrazine hydrate in a mixture of dioxan and dimethylformamide (DMF). Each synthetic operation was separated and followed by thorough washing with dichloromethane, propan-2-ol and again dichloromethane to swell, shrink and then reswell the resin. In the coupling step of the first cycle BOC-methionine (3 equivalents) was added to the resin using dicyclohexylcarbodiimide (DCCI) in the presence of pyridine (giving a substitution of 0.4 m mole/g after 3 hours reaction). Unreacted phenolic-hydroxyl groups were blocked by two acetylation steps using acetic anhydride—triethylamine in DMF. Acid deprotection was accomplished with 50% trifluoroacetic acid in dichloromethane containing 2% diethyl phosphite and 2% 1,2-ethanedithiol (1 min prewash, then 15 minutes and this process repeated after washing). The methionine phenyl ester resin trifluoroacetate salt was exchanged, using 0.075 M hydrogen chloride in DMF, to the hydrochloride salt. In the coupling step of the second cycle a mixture of BOC-phenylalanine (4 equivalents) and DCCI (4.4 equivalents) in dichloromethane was added, followed by N-methylmorpholine (2 equivalents). The neutralisation of the resin in the presence of preactivated BOC-aminoacid eliminated the slight peptide loss from the resin which is sometimes observed in the base wash and coupling steps of the usual solid phase method, and improved the quality of the crude product. BOC-glycine was added similarly in the third and fourth cycles of synthesis; but in the fifth cycle after acid deprotection the resin was twice neutralised in a separate base wash stage with triethylamine in dichloromethane, and BOC-tyrosine coupled using DCCI in the presence of 1-hydroxy-benzotriazole. Each coupling was performed for two hours and its completeness checked using the fluorescamine test.

Over 90% cleavage of the peptide from the resin occurred, with no sulphoxidation, when the completed peptide resin was treated with 50% dimethylaminoethanol in DMF for two days. Hydrolysis at pH9.7 of the labile peptide ester generated in the transesterification step, followed by chromatography on Sephadex LH 20 in DMF, gave BOC—Tyr—Gly—Gly—Phe—Met—OH (I) in 58% overall yield based on the amount of methionine originally coupled to the resin.

Alternatively treatment of the pentapeptide I phenyl ester resin with ammonia in 1:1 methanol DMF mixture gave, after 2 days, a quantitative liberation of the corresponding peptide amide.

All peptides described herein had amino-acid analyses within 7% of theoretical value and were homogeneous by thin layer chromatography (tlc) in at least three different systems. Deptrotection of peptide I with aqueous trifluoroacetic acid under nitrogen gave, after chromatography on Sephadex G25 SF in 50% aqueous acetic acid (containing 0.01% mercaptoethanol), the desired product in 48% overall yield. The methionine enkephalin obtained was shown to be chromatographically and biologically identical to authentic material prepared by conventional solution synthesis.

DETAILED SYNTHESES—EXAMPLES

The first novel analogue we synthesised, described fully below, was tyrosyl-5-aminopentanoyl-phenylalanylmethionine amide H212. BOC-5-aminopentanoic acid was coupled in the third cycle of the procedure, and the BOC-tyrosine in the fourth (last) cycle. The BOC-5-aminopentanoic acid (m.p. 47.5–48.5° from diisopropyl ether—40°-60° petroleum ether) was prepared in 70% yield by the reaction of BOC-azide and 5-aminopentanoic acid in DMF in the presence of tetramethylguanidine. After ammonolysis of the completed peptide resin, the peptide amide was chromatographed and deprotected. The desired peptide H212 was obtained in 80% overall yield. In this analogue the peptide bond —CO—NH— between $^2$Gly and $^3$Gly can be regarded as being replaced by —CH$_2$—CH$_2$—. In the second analogue prepared 5-t-butoxycarbonylamino-6-(4-hydroxyphenyl)-hexanoic acid was coupled in place of BOC—²Gly—OH in the solid phase procedure, and the addition of BOC—¹Tyr—OH omitted. The completed analogue 5-amino-6-(4-hydroxyphenyl)-hexanoyl-glycyl-phenylalanyl-methionine amide H211 was obtained in 40% overall yield (the lower yield than obtained for analogue H212 is a reflection of the low incorporation obtained in the final coupling).

EXAMPLE 1

Analogue III - H211

Structure:-

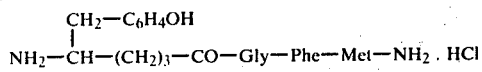

Synthesis:-

(a) 5-tert.butoxycarbonyl amino-6-(4'-hydroxyphenyl)-hexanoic acid

O-acetyl-N-phthaloyl-L-tyrosine (mp. 176–179° C. $\tau(CDCl_3)$ 0.25 (1H,S,D$_2$O-exchangeable, COO$\underline{H}$), 2.33 (4H, multiplet, phthaloyl $\underline{H}$), $\tau_A$ 2.85, $\tau_B$ 3.13 (4H, A$_2$B$_2$, J=8H$_z$, 2×ortho Ar$\underline{H}$), 4.80 (1H,t, J=8H$_z$, α-C$\underline{H}$), 6.42 (2H,d,J=8H$_z$, benzylic C$\underline{H}_2$), 7.80 (3H,S, 6COC$\underline{H}_3$). $\nu$ max (CHCl$_3$) 1780, 1750 br., 1720, 1390cm$^{-1}$ was put through three cycles of Arndt-Eistert synthesis. The phthaloyl and acetoxyl groups were removed by acid hydrolysis and the desired product obtained after reaction with tert.butoxycarbonyl-azide. $\tau$CDCl$_3$ 1.80 br. D$_2$O exchangeable, COO$\underline{H}$), $\tau_A$ 3.02 $\tau_B$ 3.26 (4H, A$_2$B$_2$, J=9H$_z$, 2×ortho Ar$\underline{H}$), ~5.3–6.5 (complex, partially D$_2$O - exchangeable, urethane N$\underline{H}$ and δ-C$\underline{H}$), 7.40 (2H,d,J=8H$_z$, benzylic C$\underline{H}_2$)~7.5–9.0 (6H, complex, 6×C$\underline{H}_2$ partly obscured by BOC Bu$^t$), 8.65 (9H,S,BOC-Bu$^t$) $\nu$max CHCl$_3$: 3600, 3440,~2600 very br., 1710, 1515 cm$^{-1}$ Found: M (mass spec.) 323; C$_{17}$ H$_{25}$ NO$_5$ requires M 323.

(b) 5-tert.butoxy-carbonylamino-6-(4'-hydroxyphenyl)-hexanoyl-glycyl-L-phenylalanyl-L-methionine phenol ester resin tert.Butoxycarbonyl-L-phenylalanyl-L-methionine phenyl ester resin (II (b) below, 0.33 g, 0.1 m mol) was subjected to the TFA deprotection, 0.075 M HCl in DMF exchange step described there. tert-Butoxycarbonylglycine (70 mg, 0.4 m mole) in CH$_2$Cl$_2$ (2.5 ml) was treated with DCCI (0.45 m mole) and added to the resin followed by N-methyl morpholine. After one hour the resin was thoroughly washed and shown to give a negative fluorescamine test. Acid deprotection (50% TFA) steps were followed by treatment with 10% triethylamine in CH$_2$Cl$_2$ (positive fluorescamine test). After thorough washing

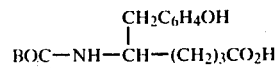

(32 mg, 0.1 m mole) in 1:1 CH$_2$Cl$_2$/DMF (3 ml) containing 1-hydroxybenzotriazole (34 mg, 0.2 m mole) was treated with DCCI (0.15 m mole) and the mixture added to the resin and allowed to react overnight. The resin was thoroughly washed and then dried to give 0.36 g.

(c) 5-Amino-6-(4'-hydroxyphenyl)-hexanoyl-glycyl-L-phenylalanyl-L-methionine amide The completed analogue phenyl ester resin (0.36 g) was converted to its amide and purified as described below (II (d)). Fractions 44–46 gave 41.7 mg of glutinous white solid, sparingly soluble in methanol, very soluble in trifluoroethanol. Tlc (silica gel) n-butanol/acetic acid/H$_2$O (3:1:1) Rf 0.71; ethyl acetate/pyridine/acetic acid/H$_2$O (80:20:6:1) Rf 0.94. The BOC-peptide analogue was deprotected under nitrogen with 80% trifluoroacetic acid, and the product chromatographed on Sephadex G25 SF as described there for (II). Fractions 28–29 were combined, evaporated and lyophilised from HCl, 25 mg of white fluffy solid. Tlc (silica gel) (i) Rf 0.50 ethyl acetate/pyridine/acetic acid/H$_2$O (60:20:6:11);

(ii) Rf 0.51 n-butanol/acetic acid/H$_2$O (3:1:1);
(iii) Rf 0.48 nPrOH/H$_2$O (7:3); Homogeneous by electrophoresis.

Amino acid analysis 6N HCl+phenol. 110° C. 18 hours gives Met 0.92; Gly 1.01; Phe 0.99 (peptide content 90%)

EXAMPLE 2

Analogue II–H212
Structure:—H—Tyr—NH—(CH$_2$)$_4$—CO—Phe—Met—NH$_2$.HCl

Synthesis:—

(a) tert.butoxycarbonyl-5-amino-pentanoic acid

5-Amino pentanoic acid (0.585 g, 5 m mol) was stirred for two days in dimethylformamide (5 ml) containing tetramethylguanidine (1.14 g, 10 m mol) and tert.butoxycarbonylazide (1.1 g, 7.5 m mol). The solution was evaporated and the residue partitioned between ethyl acetate (20 ml) and 10% citric acid solution (20 ml). The organic layer was washed with 10% citric acid (2×15 ml), water (3×15 ml) and brine 1×15 ml). Each aqueous wash was back extracted with ethyl acetate (20 ml). The combined organic layers were dried over anhydrous magnesium sulphate and evaporated to give an oil which slowly crystallised. Recrystallisation from diisopropyl ether/petrol gave 0.745 g (70% yield), mp. 47.5°–48.5° C., Rf silica gel 0.40 (benzene:dioxan:acetic acid 95:75:4).

(b) tert.butoxycarbonyl-L-phenylalanyl-L-methionine phenyl resin ester

The acetoxy resin (1.4% cross linked, 10 mole percent acetoxy-styrene) (1.0 g) was placed in the synthesis apparatus and stirred overnight with dimethylformamide:dioxan:hydrazine hydrate (10:5:1). The resin was repeatedly washed with each of the following DMF, DMF/H$_2$O (3:1), DMF, CH$_2$Cl$_2$, isopropanol, CH$_2$Cl$_2$. BOC-methionine (500 mg, 2 m mol) in dichloromethane (7.5 ml) was treated with dicyclohexylcarbodiimide (0.51 g, 2.47 m mol) and the mixture added to the resin followed by pyridine (1 ml). The coupling was allowed to stir for 3 hours; then the resin was thoroughly washed:CH$_2$Cl$_3$ (3×), iPrOH(3×), CH$_2$Cl$_2$ (3×), DMF (3×). Unreacted phenolic hydroxyl groups were acetylated by treating with acetic anhydride (1 g) and triethylamine (1.4 ml, 10 m mol) in DMF (10 ml). This was performed for ninety minutes, and then repeated again after further washing. Amino acid analysis showed 0.4 m mol/gram methionine added on to resin. The resin was then thoroughly washed and treated with 50% trifluoroacetic acid in CH$_2$Cl$_2$ (containing 2% ethanedithiol and 2% diethyl phosphite). Deprotection was for 1 minute followed by treatment for 15 minutes. This doubled treatment was again repeated after CH$_2$Cl$_2$ (3×), iPrOH (3×) and CH$_2$Cl$_2$ (3×) washes. The resin was again washed thoroughly and a small sample shown to give a strongly positive fluorescamine test. The resin was then twice washed with 0.075M HCl in DMF (10 ml for 2 minutes each time). This exchange process was repeated after thorough washing. The resin was again thoroughly washed and treated with a solution of tert.butoxycarbonyl-L-phenylalanine (0.43 g, 1.6 m mol) in CH$_2$Cl$_2$ (7 ml) to which had been added DCCI (0.36 g, 1.75 m mol). The stirred suspension was then neutralised in situ by the addition of N-methyl morpholine (80 μl). After one hour the resin was thoroughly washed and shown to give a negative fluorescamine test.

(c) BOC-L-tyrosyl-5-aminopentanoyl-L-phenylalanyl-L-methionine phenyl ester resin A sample of the dipeptide resin from (b) (0.32 g, 0.1 m mol) was deprotected and exchanged as in the coupling cycle described above. The thoroughly washed resin was treated with a solution of tert.butoxycarbonyl-5-aminopentanoic acid (0.114 g, 0.5 m mol) in CH$_2$Cl$_2$ (2.5 ml) to which had been added DCCI (0.6 m mol). The stirred suspension was neutralised in situ by the addition of N-methyl morpholine (20 μl). After one hour the resin was thoroughly washed and shown to give a negative fluorescamine test. Deprotection of the peptide resin was performed as before with 50% trifluoroacetic acid in CH$_2$Cl$_2$ containing 2% diethylphosphite and 2% ethane dithiol. After thorough washing the resin was treated with 10% triethylamine in CH$_2$Cl$_2$ (2×2 minutes). A sample was shown to give a positive fluorescamine test. The resin was again thoroughly washed and then treated with a solution of BOC-L-tyrosine (93 mg, 0.33 m mol) and 1-hydroxybenzotriazole hydrate (110 mg, 0.65 m mol) in 50% CH$_2$Cl$_2$/DMF (3 ml) to which had been added DCCI (0.6 m mol). After three hours reaction the resin was thoroughly washed and gave a very weakly positive fluorescamine test.

(d) L-Tyrosyl-5-aminopentanoyl-L-phenylalanyl-L-methionine amide

The total resin from (c) was suspended in 1:1 methanol/DMF (20 ml) and saturated at 0° C. with anhydrous ammonia. After two days at room temperature the suspension was filtered and the resin beads thoroughly washed with DMF. The combined filtrates were evaporated in vacuo to give an oily residue (137 mg, weight resin recovered 220 mg). This was dissolved in the minimum volume of dimethylformamide and applied to a column of Sephadex LH20 (94×2.5 cm). The column was eluted with DMF at a flow rate of 20 ml/hour collecting 190 drop (6 ml) fractions. Fractions 43–46 were combined and evaporated to give 77 mg. of white solid, sparingly soluble in methanol, very soluble in trifluoroethanol. Tlc (silica gel): n-butanol/acetic acid/H$_2$O (3:1:1) Rf 0.73; ethyl acetate/pyridine/acetic acid/H$_2$O (80:20:6:11) Rf 0.94; ethyl acetate/n-butanol/acetic acid/H$_2$O (1:1:1:1) Rf 0.79; nPrOH/H$_2$O (7:3) Rf 0.71. The BOC-peptide analogue was treated under nitrogen for 30 minutes with 80% trifluoroacetic acid. The solution was evaporated and the residue dissolved in deaerated 50% acetic acid containing 0.01% mercaptoethanol. The solution was applied to a column of Sephadex G 25 SF and it was eluted with the system at 8 ml/hour collecting 130 drop (4 ml) fractions. Fractions 29–31 were combined and evaporated to give a residue which on lyophilisation gave 50.7 mg of white fluffy solid; tlo (silica gel):(i) Rf 0.56 ethylacetate/pyridine/acetic acid/H$_2$O (60:20:6:11); (ii) Rf 0.54 N butanol/acetic acid/H$_2$O (3:1:1); (iii) Rf 0.49 NPrOH/H$_2$O (7:3); homogenous by electrophoresis; amino acid analysis 6 N HCl+phenol, 110° 18 hours gives Met 0.95; Tyr 1.04, Phe 1.02 (peptide content 85%). Lyophilisation from dilute hydrochloric acid afforded the hydrochloride.

EXAMPLE 3

Analogue - H215

Structure:-

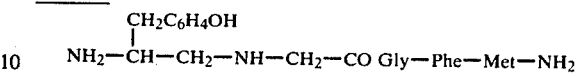

NH$_2$—CH—CH$_2$—NH—CH$_2$—CO Gly—Phe—Met—NH$_2$

Synthesis:-

(a) t.butoxycarbonyl-O-t.butyl-L-tyrosyl glycine t.butyl ester

N-t.butoxycarbonyl-O-t.butyl-L-tyrosine (2 g, 6.15 mmol) was dissolved in dimethylformamide (15 ml) and the stirred solution treated at −15° with N-methyl morpholine (0.67 ml, 6.15 mmol) and iso-butylchloroformate (0.81 ml, 6.15 mmol). After 10 minutes a precooled mixture of glycine t.-butyl ester dibenzenesulphimide salt (2.64 g, 6.15 mmol) and triethylamine (0.86 ml, 6.15 mmol) in dimethylformamide (5 ml) was added. The mixture was stirred at −10° for 30 minutes, allowed to warm to room temperature and left overnight. The reaction mixture was poured into ice cold 1 M citric acid solution; and extracted with ethyl acetate (2×50 ml). The combined organic layers were washed with 1M citric acid (2×25 ml), saturated sodium bicarbonate solution (3×25 ml) and with saturated brine (2×50 ml). The organic layer was dried over anhydrous magnesium sulphate and evaporated to give an oily residue. The residue was extracted with 40°–60° C. petroleum ether (50 ml). After 1 hour at 4° C. the supernatant liquor was decanted and evaporated. The oily residue was again extracted as previously; evaporation gave 1.13 g (41%) as an oily gum, tlc (silica gel): Rf 0.65 chloroform/methanol (95:5); Rf 0.59 benzene/dioxan/acetic (95:25:4). τ (CDCl$_3$) Σ$_A$2.84, τ$_B$3.08 (4H, A$_2$B$_2$, J=9Hz, 2×ortho Ar H), ~3.55 (1H, broad, D$_2$O exchangeable, amide NH), 4.85 (1H, α, J=8Hz, D$_2$O exchangeable, urethane NH), 5.60 (1H, multiplet, α—CH), 6.12 (2H, d, J=6Hz, Gly CH$_2$), 6.97 (2H, d, J=7Hz, Tyr β—CH$_2$), 8.55, 8.60 and 8.70 (27H, S, Boc $^t$Bu, COO$^t$Bu and O$^t$Bu).

(b) N-t.butoxycarbonyl-N-[2-t.butoxycarbonylamino, 3(4′-t.butoxyphenyl)propyl]glycine Boc-Tyr($^t$Bu)-Gly-O$^t$Bu (1.13 g, 2.5 m mol) was azeotroped with benzene and thoroughly dried. The meringue like residue was dissolved in benzene (15 ml) and treated with 70% solution of sodium dihydrobis(2-methoxyethoxy) aluminate (5 ml, 17 m mol). The mixture was heated at 83° for 1 hour, then cooled to 0° and carefully poured into ice cold 10% citric acid solution (70 ml). The solution was neutralised to pH8 with solid sodium carbonate and extracted with ether (3×60 ml). The combined ether layers were washed with ice cold 10% citric acid (3×70 ml). The combined aqueous extracts were neutralised to pH 8.5 and extracted with ether (3×100 ml) The combined ether layers from this extraction were dried over anhydrous magnesium sulphate and evaporated to give 0.65 g (71%) of the reduction product; tlc silica gel: Rf 0.44 ethyl acetate/pyridineacetic acid/H$_2$O (60:20:6:11); Rf 0.04 benzene/dioxan/acetic acid (95:25:4). τ(CDCl$_3$) τ$_A$2.90 τ$_B$3.12 (4H,A$_2$B$_2$, J=9Hz, 2×ortho Ar H), 5.3 (1H, broad, D$_2$O-exchangeable, urethane NH), ~6.2 (1H multiplet, —CH), 7.10–7.50 (6H, complex, 3×CH$_2$), 8.58 and 8.68 (18H,S, Boc $^t$Bu and O-$^t$Bu).

Approximately half the product (0.32 g, 0.9 m mol) was stirred for 4 days at room temperature in 1:1 dioxan/1M potassium bicarbonate in the presence of t. butoxycarbonylazide (0.28 g, 2 m mol). The solvents were evaporated and the residue partitioned between ether (30 ml) and water (20 ml). The ether layer was washed with water (2×20 ml) and saturated brine (2×20 ml). Each aqueous wash was back extracted with ether (20 ml). The ether solutions were further washed with ice cold 10% citric acid solution (3×20 ml), water (2×20 ml) and brine (1×10 ml). The pooled ether solutions were dried over magnesium sulphate and evaporated to give 0.27 g (63%); tlc (silica gel): Rf 0.46 benzene/dioxan/acetic acid (95:25:4); Rf 0.42 chloroform/methanol (95:5).

$\tau$(CDCl$_3$) $\tau_A$2.95, $\tau_B$3.15 (4H, A$_2$B$_2$, J=9 Hz, 2×ortho Ar H), 5.85–7.15 (5H, complex, CH and 2 CH$_2$), 7.37 (2H, d, J=6Hz, Ph CH$_2$), 8.58, 8.63 and 8.68 (27H, S, 2×Boc $^t$Bu and O$^t$Bu).

Most of the tri-Boc derivative (0.26 g, 0.52 m mol) was dissolved in pyridine (5 ml); water (2.5 ml) and potassium permanganate (0.5 g) were added, and the mixture vigorously stirred for three days. The pyridine was evaporated and the residue partitioned between ethyl acetate (40 ml) and ice cold citric acid solution (30 ml). The organic layer was washed with citric acid, water and brine; each aqueous phase was back extracted with ethyl acetate. The combined organic layers were dried over magnesium sulphate and evaporated to give a residue (0.2 g). This crude product was dissolved in ether (20 ml) and extracted with 3% aqueous ammonia (4×15 ml); each extract was back washed with ether (15 ml). The combined aqueous phases were acidified to pH3 with solid citric acid and extracted with ethyl acetate (50 ml, 25 ml). The combined organic phases were washed with water and brine, then dried over magnesium sulphate and evaporated. The residue (122 mg) was applied to a preparative silica plate and run in benzene/dioxan/acetic acid (95:25:4). The gel bands corresponding to the two U.V. absorbing products were scraped from the plates and thoroughly extracted with ethyl acetate. The organic phases were evaporated. The top band (Rf 0.47) was identified as 4-t.butoxy-benzoic acid: the lower band (Rf 0.32) as the required product 57 mg (22%); tlc (silica gel): Rf 0.47 benzene/dioxan/acetic (95:25:4); Rf 0.05 chloroform/methanol (95:5). $\tau$(CDCl$_3$) 1.30 (1H, broad, COOH), $\tau_A$2.95, $\tau_B$3.18 (4H, A$_2$B$_2$, J=9Hz 2×ortho Ar H), ~5.85–~7.1 (5H, complex CH and 2CH$_2$), 7.30 (2H, d, J=6Hz, benzylic CH$_2$), 8.60, 8.65 and 8.70 (27H, S, 2 Boc $^t$Bu and O$^t$Bu).

(c) N-[2-amino, 3-(4'-hydroxyphenyl)propyl]glycyl-glycyl-L-phenylalanyl-L-methionine amide (H215)

Starting from Boc-methionine phenyl ester resin (0.364 g, 0.15 m mol); glycyl-L-phenylalanyl-L-methionine phenyl ester resin was prepared as described in Example 2, p. 15–16, provisional patent application No. 29207/1977. After thorough washings,

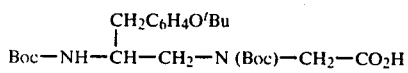
Boc—NH—CH—CH$_2$—N (Boc)—CH$_2$—CO$_2$H (47 mg, 0.095 m mol) in 1:1 CH$_2$Cl$_2$/DMF (2 ml) containing 1-hydroxy benzotriazole (34 mg, 0.2 m mol) was treated with DCCI (0.15 m mol) and the mixture added to the resin and thoroughly stirred overnight. The resin was washed with DMF (3×), CH$_2$Cl$_2$ (3×), isopropanol (3×), CH$_2$Cl$_2$ (3×); 10% triethylamine in CH$_2$Cl$_2$ (2×), and CH$_2$Cl$_2$ (4×). Remaining amino groups were blocked by reaction with acetyl imidazole (0.2 g, 2 m mol) in DMF (5 ml) for 1 hour. The resin was thoroughly washed with DMF, CH$_2$Cl$_2$, isopropanol, CH$_2$Cl$_2$ and methanol. The dried resin weighed 0.413 g.

One half of the resin (0.206 g) was stirred at 0° in 1:1 methanol/DMF (20 ml). The suspension was saturated with anhydrous ammonia; the flask tightly stoppered and stirred at room temperature for two days. The suspension was filtered and the resin beads washed with 1:1 methanol/DMF and then DMF. The combined filtrates were evaporated and the residue redissolved in DMF (1 ml). The solution was applied to a column of Sephadex LH 20 (90×2.5 cm), and eluted with DMF at a flow rate of 15 ml/hr collecting 190 drop (6 ml) fractions. Fractions 36–39 were pooled and evaporated to give 30.9 mg of pure protected peptide, tlc (silica): Rf 0.5 choroform/methanol (9:1), Rf 0.95 EtOAc/n-butanol/acetic acid/H$_2$O (2:1:1:1).

The protected peptide was dissolved in 80% trifluoroacetic acid under nitrogen. After 2 hours the solvents were evaporated in vacuo and the residue chromatographed on a column of Sephadex G25 Sf (95×1.5 cm) in 50% deaerated acetic acid (containing 0.01% mercaptoethanol) at 12 ml/hr collecting 130 drop (4 ml) fractions. Fractions 24–28 were combined and evaporated to give 22 mg of peptide. This was dissolved in deaerated 0.01M ammonium acetate pH7 (1 ml) and applied to a column (40×1 cm) of Whatman CM 52. The column was eluted at 10 ml/hr with 0.01M buffer collecting 70 drop (4.3 ml) fractions. After the first fraction a linear gradient over two days to 0.2 M ammonium acetate was commenced. Fractions 38–41 were pooled and lyophilised to give 9.6 mg; tlc (silica gel) Rf 0.40 ethyl acetate/pyridine/acetic acid water (60:20:6:11), Rf 0.64 ethyl acetate/n-butanol/acetic acid/H$_2$O (1:1:1:1).

Amino acid analysis:— 4M CH$_3$SO$_3$H 115° 24 hours Peptide content 86% Gly 1.03, Phe 0.97, Met 1.00 (determined in a parallel 6N HCl hydrolysis).

EXAMPLE 4

Analogue - H216

Structure:-

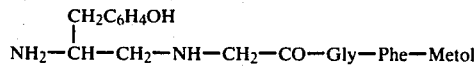
NH$_2$—CH—CH$_2$—NH—CH$_2$—CO—Gly—Phe—Metol

Synthesis:

The protected isostere peptide resin (see H215, section C; 0.206 23.3 was stirred for 2 days in 1:1 methanol/DMF (20 ml) in the presence of triethylamine (1 ml). The suspension was filtered and the resin beads thoroughly washed with 1:1 methanol/DMF, and then DMF. The combined filtrates were evaporated and the residue chromatographed on a column (90×2.5 cm) of Sephadex LH20 in DMF eluted at a flow rate of 15 ml/hr collecting 190 drop (6 ml) fractions. Fractions 38–40 were combined and evaporated to give 23.3mg of the peptide methyl ester; tlc silica gel: Rf 0.9 ethyl acetate/n-butanol/acetic acid/water (2:1:1:1), Rf 0.66 chloroform/methanol (9:1).

The peptide was dissolved in methanol (1 ml). Water (1 ml) and sodium borohydride (37 mg) were added and the mixture stirred overnight; tlc showed in chloroform/methanol (9:1) complete reduction - new spot at Rf 0.5, no spot at RF 0.66. The solvents were evaporated and the dried residue treated under nitrogen with 80% trifluoroacetic acid. After 2 hours the solvents were evaporated and the residue dried in vacuo.

The residue was dissolved in deaerated 50% acetic acid and chromatographed on a column (95×1.5 cm) in 50% deaerated acetic acid (containing 0.01% mercaptoethanol) at 12 ml/hr collecting 130 drop (4 ml) fractions. Fractions 23–27 were combined and evaporated to give a residue of 22 mg. This was dissolved in deaerated 0.01 M ammonium acetate pH7 and applied to a column (40×1 cm) of Whatman CM52. The column was eluted at 10 ml/hr with 0.01 M buffer collecting 70 drop (4.3 ml) fractions. After the first fraction a linear gradient over two days to 0.2 M ammonium acetate pH7 was commenced. Fractions 39–43 were pooled and lyophilised to give 9.6 mg; tlc (silica gel):Rf 0.42 ethylacetate/pyridine/acetic acid/water (60:20:6:11); Rf 0.66 ethyl acetate/n-butanol/acetic acid/water (1:1:1:1).

Amino acid analysis:—4 M methane sulphonic acid 115° 24 hours. Peptide content 100% Gly 1.07, Phe 0.93, methionine absent.

EXAMPLE 5

Analogue - H222
Structure:-H—Tyr—NH—CH$_2$CO—CH$_2$CH$_2$—CO—Phe—Met—Oh;
Name:- 4-(N-Tyrosylamino), 3-oxopentanoyl-L-phenylalanyl-L-methionine
Synthesis:-

(a) 4-(N-t.butoxycarbonylamino), 3-oxopentanoic acid

Boc-glycine (1.26 g, 7.2 m mol) and N-methylmorpholine (0.79 ml, 7.2 m mol) in ethyl acetate (30 ml) were treated at −10° with iso-butylchloroformate (0.95 ml, 7.2 m mol). After seven minutes the suspension was filtered into an ice cold flask and the precipitate washed with precooled ethyl acetate (5 ml). A solution of diazomethane in ether (15.8 m mol in 150 ml) was added, and the solution kept at 4° C. overnight. Evaporation of the solvents gave diazoketone (I) (see Scheme 1 below). I.R. spectrum $\nu_{max}$(CHCl$_3$) 2100 cm$^{-1}$. One half of this product in ethyl acetate (36 ml) was treated with 0.07 M hydrogen bromide in ethyl acetate (56.5 ml, 4 m mol). The solvents were evaporated and the bromoketone (II) dried thoroughly over potassium hydroxide in vacuo. Most of the product (3.2 m mol) was treated in dry benzene (6.5 ml) with triethylamine (20μl) and then with triphenylphosphine (0.85 g, 3.24 m mol). The solution was stirred overnight at room temperature. The solvent was evaporated and the pure keto-triphenylphosphonium bromide (III) (1.00 g, 60% overall) obtained as white crystals from methanol/ether; m.p. 111–115° C. (with decomp); $\nu_{max}$ (CHCl$_3$): 1725, 1695 cm$^{-1}$; $\tau$(CDCl$_3$): 2.33 (15H, multiplet, PPh$_3$), ca. 3.0–4.5 (3H, complex, D$_2$O-exchangeable, N$\underline{H}$ and COC$\underline{H}_2$), 5.70 (2H,d,J=6Hz, C$\underline{H}_2$), 8.6 (9H, s, Boc t Bu).

A suspension of (III) (0.51 g) in ethyl acetate (10 ml) was stirred vigorously overnight with 1 M sodium carbonate solution (10 ml). The organic layer was separated and the aqueous phase again extracted with ethyl acetate. The combined extracts were washed with saturated brine, dried, and evaporated in vacuo to give the pure ylide (IV) as a white crystalline solid (0.43 g, 100%); $\nu_{max}$(CHCl$_3$): 1700, 1545 cm$^{-1}$; $\tau$(CDCl$_3$): 2.57 (15 H, multiplet, PPh$_3$), 4.60 (1H, br., D$_2$O-exchangeable, N$\underline{H}$), 6.10 (2H, d, J=5Hz, C$\underline{H}_2$), 6.65 (1H, br., COC$\underline{H}$), 8.59 (9H,s, Boc-t Bu).

A solution of ylide (IV) (0.32 g, 0.74 m mol) and ethyl bromoacetate (1.23 g, 7.4 m mol) in dry DMF(7.40 ml) was stirred vigorously under N$_2$ at 80° C. for 2 hours with anhydrous sodium carbonate (1.51 g). The DMF was evaporated in vacuo and the residue partitioned between ethyl acetate and water. The organic phase was washed with water and saturated brine, then dried and evaporated in vacuo to give a pale yellow gum. The material was purified by preparative thin layer chromatography using ethyl acetate/acetone/benzene (1:2:3) for development. Elution with ethyl acetate afforded pure ylide (V) as an almost colourless gum (0.074 g, 20%); $\nu_{max}$(CHCl$_3$): 1725, 1700, 1537 cm$^{-1}$; $\tau$(CDCl$_3$): 2.48 (15H, multiplet, PPh$_3$), 4.26 (1H, br., D$_2$O- exchangeable, N$\underline{H}$), 5.6-6.1 (6H, complex, 2×C$\underline{H}_2$ and COOC$\underline{H}_2$CH$_3$), 8.60 (9H, s, Boc t Bu), 8.90 (3H, t, J=7Hz, COOCH$_2$C$\underline{H}_3$). The total product (0.145 m mol) was converted into its hydrochloride and electrolysed in 1:1 acetonitrile/deaerated water (30 ml) under N$_2$ at 25 V using mercury and platinum electrodes. After 1 hour at room temperature the solution was evaporated and the residue chromatographed on a column (67×3.2 cm$^2$) of Sephadex LH20 using methanol as eluant. The keto-ester (V) eluted in fractions 49–51 (the column was run at 12 ml/h collecting 6 ml fractions); tlc: Rf 0.53, benzene/dioxan/acetic acid (95:25:4). The product was dissolved in methanol (0.72 ml) and saponified for 2 hours at room temperature by the addition of 0.2 M sodium hydroxide solution. Pure keto-acid VI was obtained after acidification and extraction as a white solid (0.019 g, 57% over the last two steps); tlc (silica) Rf 0.39 benzene/dioxan/acetic acid (95:25:4); $\tau$(CDCl$_3$): 1.12 (1H, S, D$_2$O-exchangeable, COO$\underline{H}$), 4.55 (1H, br, D$_2$O-exchangeable, N$\underline{H}$), 5.87 (2H, d, J=5.5Hz, NH-C$\underline{H}_2$), 7.27 (4 H, S, 2×C$\underline{H}_2$), 8.55 (9H, S, Boc t Bu).

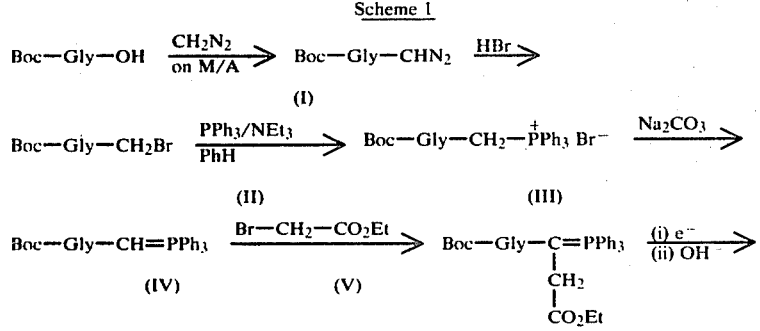

Scheme 1

Boc—NH—CH₂—CO—CH₂—CH₂—CO₂H (VI)

The above is a generally applicable method. A synthesis of (VI) by alternative non-general route is as follows. As shown in Scheme 2 below succinic anhydride is heated in dry ethanol to afford a half ester. The resulting mono-acid function is transformed into its diazoketone by the action of diazomethane on the mixed anhydride, and this is then converted to the bromoketone, these last two reactions being performed similarly to analogous reactions previously described. Treatment of the bromoketone with potassium phthalimide in DMF at 60° gives the phthalimido-ester which can be converted to the desired keto-acid (IV) by acidic hydrolysis followed by reprotection by reaction with Boc-azide.

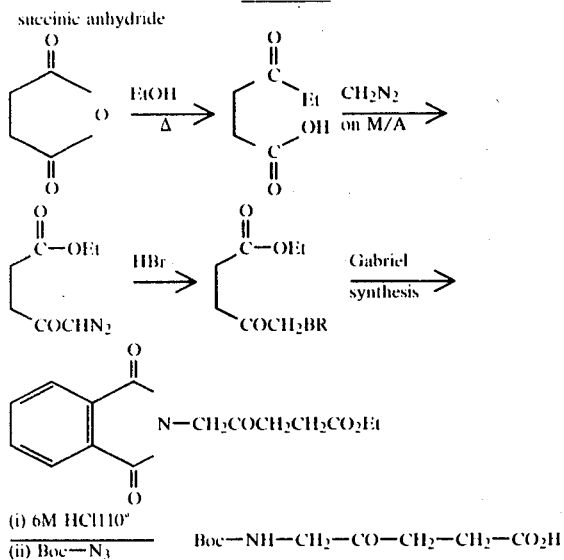

Scheme 2

(b) Synthesis of H—Tyr—NH—CH₂—CO—CH₂—CH₂—CO—Phe—Met—OH

Starting from Boc-methionine phenyl ester resin (0.205 g, 0.082 m mol), Boc-Phe-Met-resin was prepared as described in Example 2, (b) and (c). After deprotection as usual, and treatment with 10% triethylamine in CH₂Cl₂ the free base from resin gave a positive fluorescamine test. Boc—NHCH₂COCH₂CH₂CO₂H (VI, 19 mg. 0.082 m mol) and 1-hydroxybenzotriazole (27.5 mg, 0.16 m mol) in 1:1 CH₂Cl₂/DMF (2.5 ml) were treated with DCCI (0.12 m mol) and added to the resin. The incorporation of isostere was allowed to proceed overnight. The resin still gave a positive fluorescamine test and was acetylated with acetyl imidazole (fluorescamine test negative). After acid deprotection using doubled treatment with 50% trifluoroacetic acid in CH₂CL₂ containing 2% diethyl phosphite only, a positive fluorescamine test was obtained indicating successful incorporation. Boc-L-tyrosine was added, as previously, in the last cycle of synthesis (fluorescamine test negative). The resin was stirred for 2 days in 1:1 dimethylaminoethanol/DMF (20 ml). The suspension was filtered and the beads thoroughly washed with DMF. The combined filtrates were evaporated in vacuo and the residue dissolved in 1:1 DMF/water (16 ml). The solution was maintained in pH 9.7 overnight by the addition of 0.1 M sodium hydroxide solution. Water (8 ml) was added and the mixture acidified to pH 3.2 by the addition of potassium bisulphate solution. The solution was evaporated to dryness in vacuo and the residue extracted into a small volume of DMF which was chromatographed on Sephadex LH 20 in DMF (as described in Example 3, (c). Fractions 43–46 were pooled and evaporated in vacuo to give 16.2 mg of the Boc-peptide; tlc (silica): Rf 0.75 ethyl acetate/pyridine/acetic acid/water (60:20:6:11). The total product was dissolved in 80% aqueous trifluoroacetic acid under nitrogen. After 30 minutes the solution was evaporated in vacuo, and the residue chromatographed on Sephadex G25 SF as described in Example 3, (c). Fractions 26–29 were pooled, evaporated and the residue further purified on a column (1×32 cm) of SP Sephadex C25 (triethylamine form) eluted at 10 ml/hr collecting 100 drop fractions with a linear gradient from 0.01 M triethylamine formate pH5 to 0.5 M triethylamine formate pH 6.9. The desired product (7 mg) was isolated from fractions 13–14 by lyophilisation: tlc (silica) Rf 0.32 (ethyl acetate/pyridine/acetic acid/water (60:20:2:11).

Amino acid analysis 6 M HCl 110° 18 hours, peptide content 80%, Tyr 0.50; Phe 1.03; Met 0.97.

EXAMPLES 6 to 8

Analogues—H218, H219 and H220
Structures:—
H218   H—Tyr—NH—CH₂—CH₂—NH—CH₂—CO—Phe—Met—OH
H219   H—Tyr—NH—CH₂—CH₂—NH—CH₂—CO—Phe—Metol
H220   H—Tyr—NH—CH₂CH₂—NH—CH₂—CO—Phe—Met—NH₂

Synthesis:

(a) N-benzyloxycarbonyl-N-(2-t.butoxycarbonylaminoethyl)glycine

2-Bromo-N-t.butoxycarbonylaminoethane (prepared by treatment of 2-bromoethylamine hydrochloride with Boc-azide and triethylamine in DMF; 0.9 g, 4 m mol) was stirred in dry DMSO (10 ml) with glycine ethyl ester hydrochloride (1.4 g, 10 m mol) and triethylamine (1.95 ml, 14 m mol) for 2 days at 37°. The mixture was partitioned between 1 M sodium bicarbonate and ethyl acetate, and the organic extract dried and evaporated. Purificatin on Sephadex LH 20 in methanol (as described above) gave from fractions 25-26 N-(2-t.butoxycarbonylaminoethyl) glycine ethyl ester (0.31 g, 32% yield); tlc Rf 0.54 butanol/acetic acid/water (3:1:1). A sample (0.25 g, 1 m mol) was stirred with benzyl chloroformate (0.17 ml, 1.5 m mol) in dioxan (5 ml) and 1 M potassium bicarbonate solution (5 ml) at room temperature overnight. Excess reagent was destroyed by reaction with unsym.-dimethylethylenediamine (0.11 ml, 1.00 m mol) for 1 hour, and the product ethyl ester isolated by ethyl acetate extraction of the acidified reaction mixture. Hydrolysis in methanol (15 ml) with 0.2 M sodium hydroxide solution (0.5 ml) gave, after recrystallisation from ethyl acetate -60°-80° petroleum ether, the desired derivative 0.23 g (61% for last 2 steps);

mp.91.5–95°, tlc (silica) Rf 0.22 benzene/dioxan/acetic acid (95:25:4); Rf 0.05 chloroform/methanol (9:1).

(b) Boc—Tyr—NH—$CH_2$—$CH_2$N(Z)$CH_2$CO—Phe—Met phenolic resin ester (Z=benzyloxycarbonyl; Boc=t-butoxy carbonyl as before)

Boc-methionine phenyl ester resin (0.555 g, 0.22 m mol) was doubly deprotected (as usual), and after thorough washing (fluorescamine test positive), treated with 10% triethylamine in $CH_2Cl_2$ (4×20 secs). After rapid washing, there is added immediately a solution prepared 2 minutes previously at 4° of Boc-phenylalanine (0.265 g, 1 m mol) and HOBt (0.34 g, 2 m mol) in 1:1 DMF/$CH_2Cl_2$ (7 ml) treated with DCCI (0.22 g, 1.1 m mol). After 90 minutes the resin was washed with DMF (3×), $CH_2Cl_2$ (3×), iPrOH (3×) $CH_2Cl_2$ fluorescamine test negative). The resin was washed with 10% triethylamine in $CH_2Cl_2$ (4×20 seconds), thoroughly washed and reacted with acetyl imidazole (0.3 g, 3 m mol) in DMF (7 ml). After 30 minutes the resin was washed as after coupling step. In the next cycle the resin was doubly deprotected, washed (fluorescamine test positive) and repeatedly treated with 10% triethylamine in $CH_2Cl_2$ (4×20 seconds). After rapid washing, there was immediately added a solution of Boc—NH—$CH_2$—$CH_2$—N(Z)—$CH_2$—$CO_2H$ (100 mg, 0.28 m mol) and HOBt (96 mg, 0.56 m mol) in 1:1 DMF/$CH_2Cl_2$ (5 ml) at 0° treated 2 minutes previously with DCCI (83 mg, 0.4 m mol). The reaction was left overnight. After thorough washing the fluorescamine test was faintly positive. The resin was treated with 10% triethylanine in $CH_2Cl_2$ (4×20 seconds), thoroughly washed and reacted for 1 hour with acetyl imidazole. The resin was washed (fluorescamine test negative) and deprotected with 25% trifluoroacetic acid in $CH_2 Cl_2$ containing 2% ethanedithiol and 2% diethyl phosphite (for 1 minute, and then for 30 minutes). After thorough washing (fluorescamine test positive) the resin was treated with 10% triethylamine in $CH_2Cl_2$ (4×20 seconds), rewashed, and then Boc-tyrosine (0.29 g, 1 m mol) was coupled as previously. The resin was washed thoroughly (fluorescamine test negative) and dried to give 0.707 g.

(c) H 218 One third of the resin was treated with dimethylaminoethanol and the labile peptide ester hydrolysed as described previously. After chromatography on Sephadex LH 20 in DMF the peptide acid was deprotected for 30 minutes in liquid HF at 0° in the presence of amisole (1 ml) and methionine (100 mg). Chromatography on Sephadex G25 SF and Whatman CM 52 gave 14.8 mg of H218; tlc Rf 0.54 ethyl acetate/pyridine/acetic acid/$H_2O$ (50:20:6:11), Rf 0.70 ethyl acetate/n butanol/acetic acid/water (1:1:1:1). Amino acid analysis: Tyr 1.00, Phe 1.01; Met 0.84; Aminoethylglycine 0.99.

(c) H219 A further third of the resin was treated which methanol and di-isopropylethyl amine to give the free peptide methyl ester which was reduced as described for H216. Chromatography and deprotection as for H218 gave 18.5 mg of the desired product; tlc (silica) Rf 0.67 ethyl acetate/pyridine/acetic acid/water (50:20:6:11), Rf 0.73 ethyl acetate (n butanol/acetic acid/water (1:1:1:1). Amino acid analysis, Tyr 1.01; Phe 0.94, Aeg 1.05, methionine absent.

(c) H220 Transamidation of the remaining resin and the usual chromatography and deprotection procedures gave 20 mg of H220, tlc (silica) Rf 0.65 ethyl acetate/pyridine/acetic acid/water (50:20:6:11), Rf 0.69 ethyl acetate 1 n butanol/acetic acid/water (1:1:1:1).

Amino acid analysis: Tyr 1.03, Phe 0.94, Met 0.99; Aeg 1.04.

We claim:
1. Compounds having the general formula

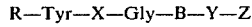

R—Tyr—X—Gly—B—Y—Z where
(a) —X is a Gly or any D-amino acid residue
—B is a Phe or N-methyl Phe residue
—Y is Leu, Met (as such or in the form of its sulphoxide), Pro, or Hypro, or formal derivatives thereof in which the carbonyl oxygen of the terminal carboxyl group is replaced by hydrogen atoms
—Z is NHR or OR
(b) The peptide link between one or more of the residues is represented by a group or groups the same or different selected from dimethylene, methylene-imino and ketomethylene groups.
(c) R is hydrogen or methyl, ethyl, propyl, cyclopropyl, butyl, allyl or other protective aliphatic group.

2. Compounds according to claim 1, wherein X is Gly, D-Ala or D-Met.

3. Compounds according to claim 1 or 2, wherein the Phe or N-methyl Phe residue representing B is substituted with a hydroxy group or halogen in the aromatic ring.

4. Compounds according to claim 1 or 2, wherein Y is Leu, Met (as such or in the form of its sulphoxide), Pro, or Hypro, or formal derivatives thereof in which the carbonyl oxygen of the terminal carboxyl group is replaced by hydrogen atoms.

5. Compounds according to claim 1, wherein one or more of the remaining peptide links and/or any methylene-imino group(s) present is in N-substituted form carrying a methyl, ethyl, propyl, cyclopropyl, butyl, allyl or other protective aliphatic group.

6. The compound $NH_2$—CH($CH_2C_6$ $H_4OH$)—$CH_2$—$CH_2$—$CH_2$—CO—Gly—Phe—Met—$NH_2$.

7. The compound H-Tyr—NH—$CH_2$—$CH_2$—$CH_2$—$CH_2$—CO—Phe—Met—$NH_2$.

8. The compound $NH_2$—CH($CH_2C_6H_4OH$)—$CH_2$—NH—$CH_2$—CO—Gly—Phe—Met—$NH_2$.

9. The compound $NH_2$—CH($CH_2C_6H_4OH$)—$CH_2$—NH—$CH_2$—CO—Gly—Phe—Metol.

10. The compound H-Tyr—NH—$CH_2$—CO—CH$_2$—$CH_2$CO—Phe—Met—OH.

11. The compound H-Tyr—NH—$CH_2$—$CH_2$—NH—$CH_2$—CO—Phe—Met—OH.

12. The compound H—Tyr—NH—$CH_2$—$CH_2$—NH—$CH_2$—CO—Phe—Metol.

13. The Compound H—Tyr—NH-$CH_2$—$CH_2$—NH—$CH_2$—CO—Phe—Met—$NH_2$.

14. A pharmaceutical composition comprising as the active ingredient compounds of claim 1 or pharmaceutically acceptable N-protected or salt forms thereof in a pharmaceutically acceptable diluent or carrier.

15. A pharmaceutical composition according to claim 14 wherein the active ingredient is a compound wherein X is gly D-ala or D-met.

16. A pharmaceutically active composition according to claim 14 wherein the active ingredients is a compound wherein the Phe or N-methyl Phe residue representing B is substituted with a hydroxy group or halogen in the aromatic ring.

17. A pharmaceutical composition according to claim 14 wherein the active ingredient is a compound wherein Y is Leu, Met (as such or in the form of its sulphoxide), Pro, or Hypro, or formal derivatives thereof in which the carbonyl oxygen of the terminal carboxyl group is replaced by hydrogen atoms.

18. A pharmaceutical composition according to claim 14 wherein the active ingredient is a compound wherein one or more of the remaining peptide links and/or any methylene-imino group(s) present is in N-substituted form carrying a methyl, ethyl, propyl, cyclopropyl, butyl, allyl or other protective aliphatic group.

19. A pharmaceutical composition according to claim 14 wherein the active ingredient is $NH_2$—$CH(CH_2C_6H_4OH)$—$CH_2$—$CH_2$—$CH_2$—$CO$—$Gly$—$Phe$—$Met$—$NH_2$.

20. A pharmaceutical composition according to claim 14 wherein the active ingredient is H-Tyr—NH—$CH_2$—$CH_2$—$CH_2$—CO—Phe—Met—$NH_2$.

21. A pharmaceutical composition according to claim 14 wherein the active ingredient is $NH_2$—$CH(CH_2C_6H_4OH)$—$CH_2$—NH—$CH_2$—CO—Gly—Phe—Met—$NH_2$.

22. A pharmaceutical composition according to claim 14 wherein the active ingredient is $NH_2$—$CH(CH_2C_6H_4OH)$—$CH_2$—NH—$CH_2CO$—Gly—Phe—Metol.

23. A pharmaceutical composition according to claim 14 wherein the active ingredient is H—Try—NH—$CH_2$—CO—$CH_2$—$CH_2$—CO—Phe—Met—OH.

24. A pharmaceutical composition according to claim 14 wherein the active ingredient is H-Tyr—NH—$CH_2$—CO—$CH_2$—$CH_2$—CO—Phe—Met—OH.

25. A pharmaceutical composition according to claim 14 wherein the active ingredient is H-Tyr—NH—$CH_2$—$CH_2$—NH—$CH_2$—CO—Phe—Metol.

26. A pharmaceutical composition according to claim 14 wherein the active ingredient is H—Tyr—NH—$CH_2$—$CH_2$—NH—$CH_2$—CO—Phe—Met—$NH_2$.

* * * * *